United States Patent [19]

Mountz et al.

[11] Patent Number: 4,884,566
[45] Date of Patent: Dec. 5, 1989

[54] SYSTEM AND METHOD FOR DETERMINING ORIENTATION OF PLANES OF IMAGING

[75] Inventors: James M. Mountz, Ann Arbor; Mark W. Wilson, Detroit, both of Mich.

[73] Assignee: The University of Michigan, Ann Arbor, Mich.

[21] Appl. No.: 181,902

[22] Filed: Apr. 15, 1988

[51] Int. Cl.$^4$ .............................................. A61B 19/00
[52] U.S. Cl. ................................ 128/303 B; 128/898; 378/205
[58] Field of Search .................... 128/303 B, 653, 630; 378/162, 163, 177, 180, 195, 205, 208

[56] References Cited

U.S. PATENT DOCUMENTS 3,614,950 10/1971 Rabey .............................. 128/303 B
4,618,978 10/1986 Cosman .......................... 128/303 B Primary Examiner—Michael H. Thaler
Assistant Examiner—William Lewis
Attorney, Agent, or Firm—Rohm & Monsanto

[57] ABSTRACT

An apparatus for use in determining the orientation and location of an image plane, particularly when imaging the head of a human being, has an elongated flexible channel provided for containing an imaging-opaque fluid which is visible in the image. First and second carriers are each provided for supporting three respective portions of the elongated flexible channel at respective orientations transverse to the image plane and in predetermined space relation with respect to one another. Preferably, the portions of the said elongated flexible channel are arranged substantially as legs of a triangle. A support arrangement maintains the first and second carriers in fixed spatial relation to one another and to the head of the human being. The present invention can be used in any of several known imaging modalities by using appropriate contrast agents. After imaging, the portions of the said elongated flexible channel appear as points in the image, the location of the plane of imaging, and its orientation, being determined by analysis of the distance between such points, and the ratios of the distances between them. Such analysis can be performed by computer. Additionally, with the use of the present invention, computer analysis can be used to reconstruct a given set of consecutive image planes, such as from MRI, to match another given set of image planes, such as from PET.

17 Claims, 4 Drawing Sheets

RATIO = A/B

RATIO > 1

RATIO = A/B

RATIO < 1

SYSTEM AND METHOD FOR DETERMINING ORIENTATION OF PLANES OF IMAGING

Background of the Invention

This invention relates generally to imaging systems, and more particularly, to a system for forming a coordinate system in an image whereby the location and orientation of an image plane, with respect to certain anatomical features, can be determined and reproduced for subsequent imaging using the same or various other types of imaging modalities, thereby facilitating localization of other anatomical features during imaging.

Imaging machines are now commonplace in the nuclear medicine departments of many hospitals, as well as in medical research facilities. As is known, the images produced by such machines appear as a slice through a portion of the body being imaged. It is, however, a problem with such imaging systems that it is extremely difficult to reproduce a particular image. That is, after taking a first set of images, it is difficult at a later time to adjust the location of the patient or of the equipment to take a subsequent image in the same image plane as a prior image. Of course, one approach to this problem is simply to take a multiplicity of images of a given region of a body, but even this approach will not solve the problem since this approach generally would rely on axial displacement of the images with respect to the anatomical region being imaged, but would not take into consideration the many possible variations in angular orientation of the image plane. Moreover, this approach is not feasible when attempting to reproduce an image plane using different imaging modalities, particularly in view of the fact that different equipment is used for the different modalities, resulting in different slice thicknesses and appearance. The strikingly different appearance of the images resulting from the different modalities, as well as other differences, render a visual effort at matching an image plane highly impractical.

One prior art attempt at achieving the benefits of the present invention includes the placement of radioactive markers at selected positions in the body to be imaged. However, the position of such markers is not reproducible, and cannot be used in different imagers. There is a need for a system which affords reproducibility of position, is noninvasive, and can be used for a variety of imagers.

The difficulties in the present state of the art regarding reproducibility of an image plane are particularly acute in cerebral imaging. There is a need for a coordinate system for the localization of neuroanatomical features of cerebral images, and to provide anatomic images which correspond to prior functional images. Additionally, it is especially desirable to correlate images resulting from different imaging modalities. For example, it is highly desirable to correlate functional PET or SPECT images with MRI or CT images. Such images, with their distinct appearances, cannot be correlated visually. Accordingly, there is a need for a system which permits reproducibility of image planes, within a few millimeters in the x, y, and z directions.

It is, therefore, an object of this invention to provide a simple and economical system for defining the location and orientation of image planes in various types of imaging systems.

It is another object of this invention to provide an apparatus for reproducibly positioning an image plane definition system with respect to a living being.

It is also an object of this invention to provide a system for defining an image plane which can be employed in different imaging modalities.

It is a further object of this invention to a system to facilitate reproducibility of image planes, within a few millimeters in the x, y, and z directions, with reference to external anatomical landmark features on the skull and face.

It is additionally an object of this invention to provide a system which provides reproducibility of image planes for multiple tomographic modalities, such as CT, MRI, PET, and SPECT.

It is yet a further object of this invention to provide a coordinate system for defining an image plane and which does not cause discomfort to the patient when applied.

It is also another object of this invention to provide a coordinate system for a patient which will remain in place, on the patient, for an indefinite period of time.

It is yet an additional object of this invention to provide a system which affords reproducibility of images to within 1-'millimeters.

It is still another object of this invention to provide a noninvasive system for correlating image planes.

Summary of the Invention

The foregoing and other objects are achieved by this invention which provides an apparatus for defining an image plane of an image through a selected portion of the body of a being. In accordance with the invention, the apparatus is provided with a plurality of elongated channel sections for containing a material, preferably in the form of a fluid, which is visible in the image. A first carrier supports a first predetermined number of the elongated channel sections in respective orientations transverse to the image plane and in predetermined space relation with respect to one another. Also, a second carrier supports a second predetermined number of the elongated channel sections, also in respective orientations transverse to the image plane and in predetermined space relation with respect to one another. A support is provided for maintaining the first and second carriers in fixed spatial relation to one another and to the body of the being.

In a specific illustrative embodiment of the invention, the selected portion of the body of the being which is desired to be imaged is the head of the being. In this embodiment, the support means is provided with an ear coupling arrangement, illustratively in the form of an ear plug, for coupling the support arrangement to the ear of the being. This embodiment may also include a slot which is cut into the anterior portion of the base of the triangles which is placed directly over the lateral canthus. The slot and ear coupling arrangement ensures that the carriers are placed reproducibly on the head of a human being with respect to the bony anatomical landmarks, i.e., the lateral canthus and external acoustic meatus. In this manner, reproducibility of subsequent images is achieved by reference to the bony and other features of the head and face.

The first carrier is provided with first and second carrier portions for supporting respective ones of the plurality of elongated channel sections therealong, the first and second carrier portions being coupled to one another at respective first ends thereof, and to a base member at respective second ends. The first and second carrier portions and the base member are arranged, in the specific embodiment, to form a triangle. In addition, there is provided a third carrier portion arranged substantially to bisect the triangle. In an embodiment of the invention where the being is a human being, the ear coupling arrangement is coupled to the base member. With the aid of the ear coupling arrangement, the base member of a specific illustrative embodiment of the invention is situated on the head of the human being so as to be substantially parallel with the canthomeatal line.

In one embodiment, the elongated channel sections are coupled to one another to form a continuous channel having an input for receiving an imaging-opaque fluid, and an output for eliminating same. In such an embodiment, the elongated channel sections correspond to portions of a continuous length of flexible tubing.

In accordance with a further specific illustrative apparatus embodiment of the invention which is specifically for use in imaging the head of a human being, an elongated flexible channel is provided for containing an imaging-opaque fluid which is visible in the image. First and second carriers are each provided for supporting three respective portions of the elongated flexible channel at respective orientations transverse to the image plane and in predetermined space relation with respect to one another. A support arrangement maintains the first and second carriers in fixed spatial relation to one another and to the head of the human being.

In a further embodiment, the portions of the elongated flexible channel supported by each of the carriers are each substantially straight. Of course, other predeterminable contours or curves can be used in the practice of the invention. In the straight embodiment, however, the portions of the elongated flexible channel supported by the carriers are arranged substantially as legs of a triangle.

The present invention can be used in any of several known imaging modalities. For example, in embodiments where the image is to be obtained via PET, the image-opaque fluid contained in the channel may be a solution of $^{18}F$ contrast material. If the image is to be obtained via MRI, the image-opaque fluid can be a solution of Ni contrast material. When the image is to be obtained via CT, the image-opaque fluid can be a solution of I contrast material.

In accordance with a method aspect of the invention, a plurality of elongated channel members having an imaging-opaque characteristic in the vicinity of the selected portion of the body, are place in an orientation transverse to the image plane, and in predetermined space relationship to one another, whereby a distance between the elongated channel members varies in response to position of the image plane along the elongated channel members. The method further includes the steps of forming the image to include therein images of the cross-sections of the elongated channel members, and determining a location of the image plane of the image in response to the distance between the images of the cross-sections of the elongated channel members.

In one method embodiment of the invention, the step of determining includes the step of determining distances between the images of the cross-sections of the elongated channel members. Moreover, this step can include, in some embodiments, the step of determining a ratio of distances between selected ones of the images of the cross-sections of the elongated channel members.

The determination of distances and ratios of distances can be performed by computer analysis.

BRIEF DESCRIPTION OF THE DRAWING

Comprehension of the invention is facilitated by reading the following detailed description, in conjunction with the annexed drawing, in which.

DETAILED DESCRIPTION

Figure 1:
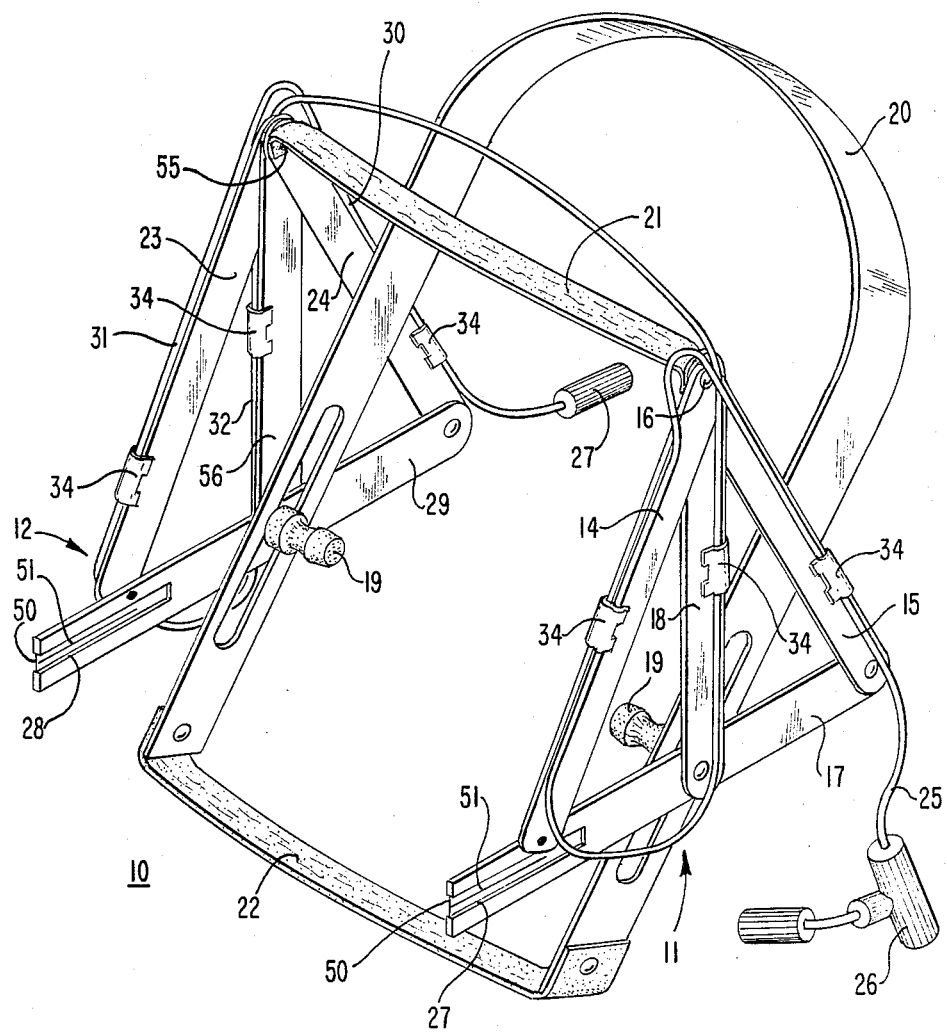
FIG. 1 is an isometric representation of a specific illustrative embodiment of the invention for use in imaging the head of a human being.

FIG. 1 is an isometric representation of a coordinate system 10 which is intended for use in the imaging of the head of a human being. As shown coordinate system 10 is provided with two triangular sections, 11 and 12. Referring to triangular section 11, two legs, 14 and 15 of a substantially isosceles triangle are coupled to one another at coupling point 16, and to a base member 17. In addition, there is provided a third leg 18 which is coupled to coupling point 16 and base member 17.

Triangular section 12 is structured similar to triangular section 11. This triangular section is provided with two legs, 23 and 24, which are coupled to one another at a coupling point 55, to form a further, substantially isosceles triangle. Triangular section 12 is further provided with a corresponding third leg 56 which is coupled to coupling point 55, and to corresponding base member 29. In addition, each of the base members, in this specific illustrative embodiment, is provided with an ear plug 19 for coupling with the ear of the human. In an advantageous embodiment, slots 27 and 28 are cut into the anterior portions of base members 17 and 29, respectively. A thin, transparent film 50 is received within slots 27 and 28. Film 50 has centerline 51 printed thereon. Centerline 51 is positioned over the corner of the eye, or the lateral canthus, of the human subject.

Triangular sections 11 and 12 are coupled to one another by a head strap 20, a first elastic strap 21, and an elastic chin strap 22. These straps are used for mounting the coordinate system on the head of the human being, and securing same in a manner which affords reproducibility of the position to within 1–2 millimeters.

Coordinate system 10 is further provided with an elongated flexible tubing 25, which is shown to be arranged along legs 14, 15 and 18 of triangular section 11. Clips 34 can be provided to the base members in order to prevent the tubing from dangling freely. In addition, flexible tubing 25 is arranged along the legs of triangular section 12 in a manner similar to that described with respect to triangular section 11. More particularly, the portion of flexible tubing 25 which is arranged to extend along leg 23 of triangular section 12 is designated in this figure as 31. The portion which extends along leg 24 is designated as 30; and the portions of flexible tubing 25 extending along third leg 56 and base member 29 are designated as 32 and 33, respectively. The flexible tubing is terminated at each end with respective ports 26 and 27 which permit and control the passage through the flexible tubing of an image-opaque fluid. Each leg of the triangular sections, in this embodiment, is provided with a straight portion of flexible tubing 25.

In an advantageous embodiment, the coordinate system of the instant invention is constructed entirely of light-weight nylon and rubber. Of course, other flexible polymeric materials can be utilized in the construction of the invention. However, use of non-magnetic materials renders the coordinate system suitable for use with all types of scanners, including MRI.

Figure 2:
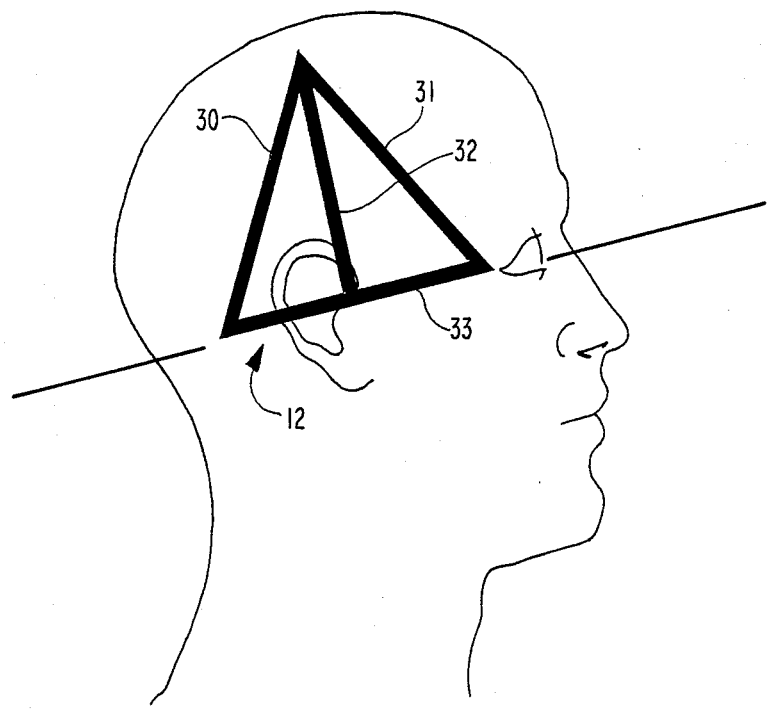
FIG. 2 is a schematic representation of the embodiment of FIG. 1 installed on the head of a human being.
Figure 3:
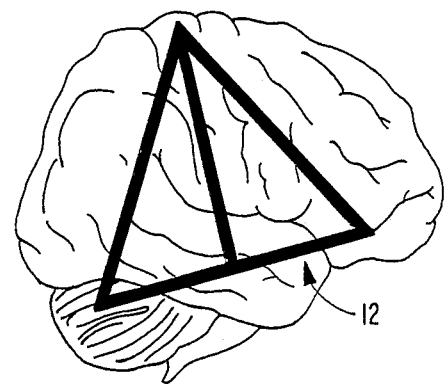
FIG. 3 is a schematic representation of the embodiment of FIG. 1 as correlated to the anatomy of the brain of a human being.

FIG. 2 is a schematic representation of the embodiment of FIG. 1 superimposed on the head of a human being. As shown, the triangular section 12 is represented as having a leg 30, a leg 31, a bisecting leg 32, and a base member 33. These elements of structure correspond to portions of flexible tubing 25, shown in FIG. 1. The base member is positioned on the side of the head so as to be parallel to cantho-meatal line 35. For purposes of illustration, triangular section 12 is represented in FIG. 3 as superimposed on a human brain. Such superimposition is stable, and responsive, in this embodiment, to external anatomical features of the head.

Figure 4:
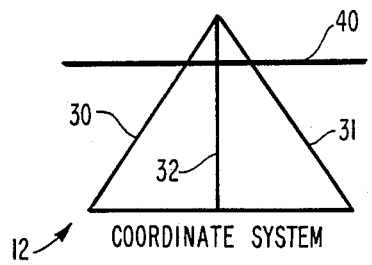
FIGS. 4 and 5 are schematic representations showing the effect of axial translation of the image plane on the resulting image.
Figure 4:
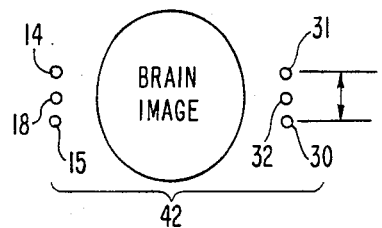
Figure 5:
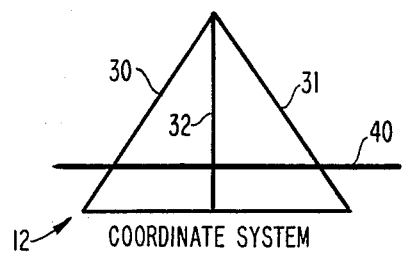
Figure 5:
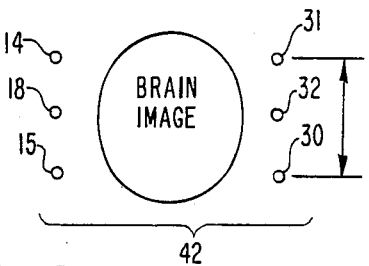

FIGS. 4 and 5 are schematic, simplified representations of the effect of axial translation of an image plane 40, which is represented cross-sectionally as a line, on a brain image 42. As shown in this figure, image plane 40 intersects legs 30, 31, and 32 near where they are joined together, and therefore they are represented cross-sectionally in brain image 42 by correspondingly designated image dots, shown on the right-hand side of the figure, which are relatively close together. Triangular section 11, which would be on the other side of the brain, is similarly represented by dots 14, 18, and 15, which correspond in their designation to the legs of triangular section 11, and are also similarly close together.

FIG. 5 is identical to FIG. 4, except that image plane 40 is disposed somewhat lower in coordinate system 12, such that it intersects legs 30, 32, and 31 where they are further apart. Correspondingly, brain image 42 shows corresponding dots 30, 32, and 31 to be spaced further apart from one another than is represented in FIG. 4. Additionally, points 14, 18, and 15, which correspond to the leg of triangular section 11 are similarly spaced further apart than represented in FIG. 4.

Figure 6:
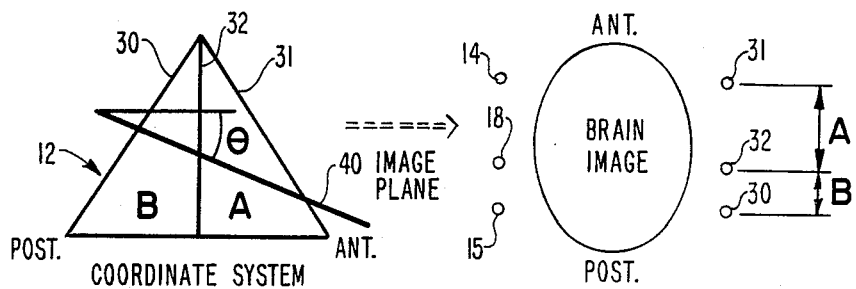
FIGS. 6 and 7 are schematic representations of the effect of angular rotation of the image plane on the resulting image.

FIG. 6 is a schematic representation similar to FIGS. 4 and 5, except that the image plane is arranged at an angle Θ through coordinate system 12. This corresponds to the head being tilted back during imaging so that the image plane is lower in the anterior, or face region, than at the back of the head. As can be seen in this figure, this angular orientation of the image plane causes dots 31 and 32 to be further apart than dots 32 and 30. The ratio of the distances, A:B, in this situation is greater than unity.

Figure 7:
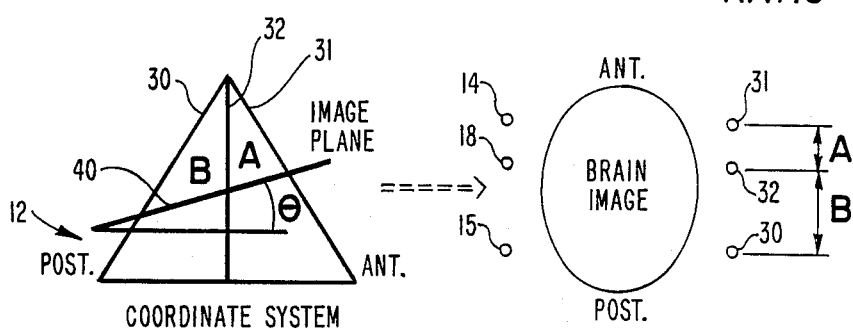

FIG. 7 is identical to FIG. 6, except that image plane 40 is arranged at an angle Θ upward, corresponding to the head being tilted forward during imaging. In this situation, the ratio A:B is less than unity. As is evident from the foregoing, when the angle Θ has a value of zero, the ratio of A:B will equal unity.

Figure 8:
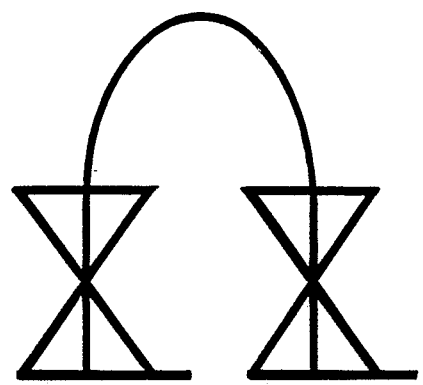
FIGS. 8 and 9 are schematic representations of alternative embodiments of the invention.
Figure 9:
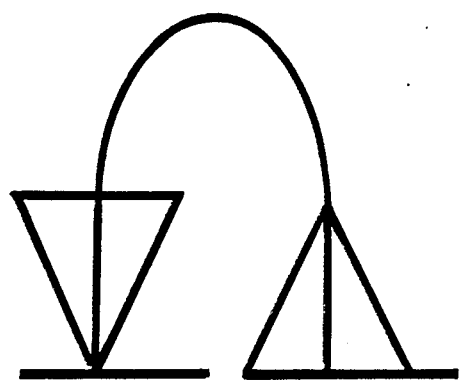

FIGS. 8 and 9 are schematic representations of variations in the coordinate system of the present invention. More specifically, FIG. 8 shows the coordinate system formed of four triangular sections, two on each side. The triangular sections on each side are inverted with respect to one another and joined together at their respective apexes.

With respect to FIG. 9, only two triangular sections are used, one on each side. However, in this embodiment, the triangles are inverted with respect to one another. Thus, the apex of one triangle is down while that of the other is up.

An advantage of the coordinate system is that computer analysis can be used to reconstruct one set of consecutive image planes, illustratively MRI images, to match another given set of consecutive images, illustratively PET images, based upon the information provided by use of the coordinate system with respect to their respective orientations.

Although the invention has been described in terms of specific embodiments and applications, persons skilled in the art can, in light of this teaching, generate additional embodiments without exceeding the scope or departing from the spirit of the claimed invention. Accordingly, it is to be understood that the drawing and description in this disclosure are proffered to facilitate comprehension of the invention, and should not be construed to limit the scope thereof.

What is claimed is:

1. An apparatus for defining the location of an image plane of an image through a selected portion of the body of a being, the apparatus comprising:

a plurality of elongated channel sections for containing a material which is visible in the image;

first carrier means for supporting a first predetermined number of said elongated channel sections in respective orientations transverse to the image plane and in predetermined space relation with respect to one another, said first carrier means being provided with respective first and second carrier portions for supporting respective ones of said plurality of elongated channel sections therealong, said first and second carrier portions being coupled to one another at respective first ends thereof, and to a base member at respective second ends, said first and second carrier portions and said base member forming a triangle, and a third carrier portion arranged substantially to bisect said triangle; and support means for maintaining said first carrier means in fixed spatial relation to the body of the being.

2. The apparatus of claim 1 wherein the selected portion of the body of the being is the head of the being, said support means comprising ear coupling means for coupling said support means to an ear of the being.

3. The apparatus of claim 2 wherein there is further provided second carrier means for supporting a second predetermined number of said elongated channel sections in respective orientations transverse to the image plane and in predetermined space relation with respect to one another, said second carrier means being provided with respectively associated first and second carrier portions for supporting respective ones of said plurality of elongated channel sections therealong, said first and second carrier portions being coupled to one another at respective ends thereof, and to a base member at respective second ends, said first and second carrier portions and said base member forming a triangle.

4. The apparatus of claim 3 wherein said second carrier means further comprises a third carrier portion arranged substantially to bisect said triangle.

5. The apparatus of claim 2 wherein the being is a human being and said ear coupling means is coupled to said base member of said first carrier means, for arranging said base member on the head of the human being so as to be substantially parallel with the cantho-meatal line.

6. The apparatus of claim 1 wherein said elongated channel sections are coupled to one another to form a continuous channel, said continuous channel having input means for receiving an imaging-opaque fluid, and an output means for eliminating said imaging-opaque fluid.

7. The apparatus of claim 6 wherein said elongated channel sections are portions of a continuous length of flexible tubing.

8. The apparatus of claim 1 wherein said first and second carrier means are formed of an imaging-transparent material.

9. A method of defining an image plane of an image with respect to a selected portion of the body of a being, the method comprising the steps of:
placing a plurality of elongated channel members having an imaging-opaque characteristic in the vicinity of the selected portion of the body, in an orientation transverse to the image plane, and configured in space relationship to one another to form substantially a bisected triangle, whereby a distance between said elongated channel members varies in response to position of the image plane along said elongated channel members;
forming the image to include therein images of the crosssections of said elongated channel members; and
determining a location of the image plane of the image in response to the distance between said images of the crosssections of said elongated channel members.

10. The method of claim 9 wherein said step of determining comprises the step of determining distances between said images of the cross-sections of said elongated channel members.

11. The method of claim 9 wherein said step of determining comprises the step of determining a ratio of distances between selected ones of said images of the cross-sections of said elongated channel members.

12. An apparatus for defining an image plane of an image through the head of a human being, the apparatus comprising:
an elongated flexible channel for containing an imaging-opaque fluid which is visible in the image;
first and second carrier means each for supporting three respective portions of said elongated flexible channel at respective orientations transverse to the image plane and in predetermined space relation with respect to one another, at least one of said carrier means being configured substantially as a bisected triangle; and
support means for maintaining said first and second carrier means in fixed spatial relation to one another and to the head of the human being.

13. The apparatus of claim 12 wherein said portions of said elongated flexible channel supported by said carrier means are each substantially straight.

14. The apparatus of claim 13 wherein said portions of said elongated flexible channel supported by each of said carrier means are arranged substantially as portions of a triangle.

15. The apparatus of claim 12 wherein the image is obtained via PET and said image-opaque fluid is a solution of 18F contrast material.

16. The apparatus of claim 12 wherein the image is obtained via MRI and said image-opaque fluid is a solution of Ni contrast material.

17. The apparatus of claim 12 wherein the image is obtained via CT and said image-opaque fluid is a solution of I contrast material.

* * * * *